United States Patent [19]

Sato et al.

[11] Patent Number: 4,691,569
[45] Date of Patent: Sep. 8, 1987

[54] APPARATUS FOR OBSERVING SOUND FIELD OF ULTRASONIC WAVE

[75] Inventors: Takuso Sato, Tokyo; Nobuyuki Ichida, Machida, both of Japan

[73] Assignee: Fujitsu Limited, Kawasaki, Japan

[21] Appl. No.: 931,981

[22] Filed: Nov. 24, 1986

Related U.S. Application Data

[63] Continuation of Ser. No. 647,389, Sep. 5, 1984, abandoned.

[30] Foreign Application Priority Data

Sep. 13, 1983 [JP] Japan ................ 58-168600

[51] Int. Cl.$^4$ ............................................ G01N 29/00
[52] U.S. Cl. .................................. 73/596; 73/599; 73/602; 73/603; 73/604; 73/606
[58] Field of Search ............... 73/596, 602, 603, 604, 73/606

[56] References Cited

U.S. PATENT DOCUMENTS

| | | | |
|---|---|---|---|
| 3,450,225 | 6/1969 | Silverman | 73/603 |
| 4,059,010 | 11/1977 | Sachs | 73/596 |
| 4,099,878 | 7/1978 | Lee | 73/596 |
| 4,495,816 | 1/1985 | Schlumberger | 73/602 |

FOREIGN PATENT DOCUMENTS 0128635 3/1984 European Pat. Off.
EP84306257 1/1986 European Pat. Off.

OTHER PUBLICATIONS

"Sonic Holography", Holder, *Electronics World*, Jun. 1970, vol. 83, No. 6, pp. 32-35.
Sachs et al., "A Two-Beam Acoustic System for Tissue Analysis", *Phys. Med. Biol.*, 1977, vol. 22, No. 2, pp. 327-340.
Zhu et al., "Determination of the Acoustic Nonlinearity Parameter B/A from Phase Measurements", *J. Acoust. Soc. Am.*, vol. 74, No. 5, Nov. 1983, pp. 1518-1521.
Sato et al., "Nonlinear Parameter Tomography, Active Incoherent and Adaptive Imaging for Ultrasonic Tissue Characterization", 1st Intnl. Symposium on Medical Imaging and Image Interpretation ISMIII '82, vol. 375, pp. 454-459.
Dunn et al., "Nonlinear Ultrasonic Wave Propagation in Biological Materials", Proceedings of the Ultrasonics Symposium, 1981, pp. 527-532.
Bjorno et al., "On the Theoretical Basis for an Application of the Nonlinear Acoustics . . . ", *Ultrasound*, 1982, pp. 167-171.
Muir, "Prediction of Nonlinear Acoustic Effects at Biomedical Frequencies and Intensities", *Ultrasound in Med. and Biol.*, vol. 6, 1980, pp. 345-357.

Primary Examiner—Howard A. Birmiel
Attorney, Agent, or Firm—Staas & Halsey

[57] ABSTRACT

An apparatus for observing a sound field of an ultrasonic wave, including a first unit which determines characteristic values of a medium at each point of a predetermined region by an ultrasonic wave having a sound field of an arbitrary form and a second unit which displays an output of the first unit as two-dimensional or three-dimensional distribution in the predetermined region, and allows control of the form of the sound field of the ultrasonic wave.

7 Claims, 8 Drawing Figures

APPARATUS FOR OBSERVING SOUND FIELD OF ULTRASONIC WAVE

This is a continuation of co-pending application Ser. No. 647,389 filed on Sept. 5, 1984, now abandoned.

BACKGROUND OF THE INVENTION (1) Field of the Invention

The present invention relates to an ultrasonic wave apparatus which converts the sound field of an ultrasonic wave, radiated by an ultrasonic vibrator into biological tissue or other medium, into a video image and also allows shape or form control of the sound field to produce any desired spatial distribution along with confirmation of the shape using video-image of the sound field, more particularly to an ultrasonic wave apparatus which uses a non-linearity characteristic of the ultrasonic wave medium.

(2) Description of the Prior Art

The conventional methods for measuring the sound field of an ultrasonic wave in an ultrasonic wave medium are the optical schlieren method and the direct hydrophone measurement method.

These methods, however, are not suitable for measuring the sound field in biological tissue or other media through which light cannot pass or through which a hydrophone cannot be moved freely.

SUMMARY OF THE INVENTION

An object of the present invention is to enable rapid, easy measurement of an ultrasonic wave sound field in an ultrasonic wave medium by a new method.

Another object of the present invention is to allow measurements of an ultrasonic wave sound field in biological tissue or other media previously unmeasurable by conventional methods.

According to the present invention, there is provided an apparatus for observing a sound field of an ultrasonic wave including first means for determining characteristic values or medium parameter of a medium at each point of a predetermined region using an ultrasonic wave having a sound field with an arbitrary form or shape and second means for displaying the output of the first means as a two-dimensional or three-dimensional distribution in the predetermined region to allow control of the form or shape of the sound field of the ultrasonic wave.

BRIEF DESCRIPTION OF THE DRAWINGS

Further features and advantages of the present invention will be apparent from the ensuing description with reference to the accompanying drawings, in which.

DESCRIPTION OF THE PREFERRED EMBODIMENTS

In view of the problems in the prior art, the inventors and others proposed to convert the sound field of the ultrasonic wave in the biological tissue and other such media into a video image using the non-linearity of the ultrasonic wave medium.

First, the principle for determining the amount $(1/\rho C)(B/A)e$ for the equivalent non-linear type parameter $(B/A)e$ will be explained. The symbol e suffix in parentheses means "equivalent". When the non-linear characteristics of a medium are taken into consideration, the sound velocity C varies according to pressure as shown in equation (a) below:

$$C = C_0 + (\tfrac{1}{2}\rho_0 C_0)\cdot(B/A)\cdot \Delta P \qquad (a)$$

where B/A, when in an equi-entropy condition is defined by equation (b) below:

$$B/A = 2\rho_0 C_0 \cdot (\partial C/\partial P)_s. \qquad (b)$$

In this case the propagation direction of the sound wave is the same as that of the pressure variation. $(B/A)e$ is the equivalent nonlinear parameter when the pressure variation is measured perpendicular to the propagation direction of the soundwave. In a uniform medium, using $\gamma$ to represent a Poisson ratio, the relationship between B/A and $(B/A)e$ is defined by equation (c) below:

$$(B/A)e = \gamma/(1-\gamma)\cdot(B/A) \qquad (c)$$

In a liquid or living tissue $\gamma = 0.5$ therefore B/A is substantially equivalent to $(B/A)e$. Additional discussion of (B/A) and (B/A)e and definitions therefore can be found in a paper presented at the 7th International Symposium on Ultrasonic Imaging and Tissue Characterization held on Jan. 6–9, 1982 by M. Ichida, T. Soto, O. Ikeda and M. Linzer entitled "Ultrasonic Imaging of the Non-Linear Parameter of Tissue Using Low Frequency Pumping Waves and High Frequency Probe Waves".

Figure 1:
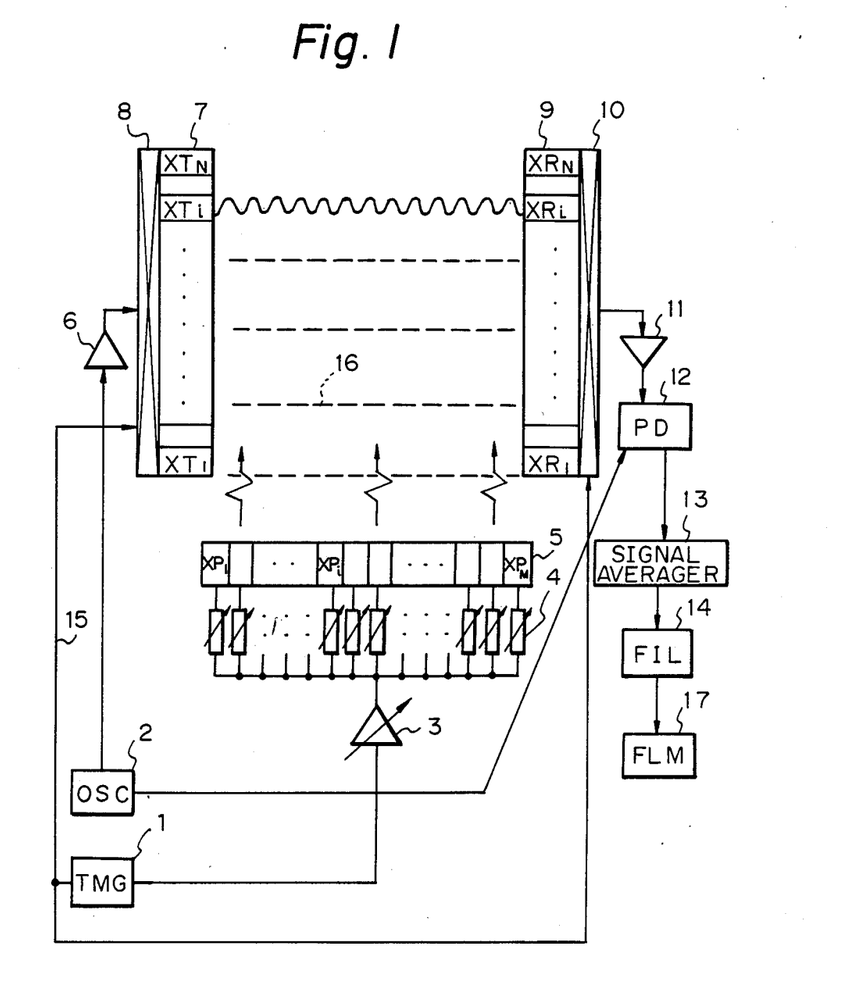
FIG. 1 is a block diagram of the principle by which a sound field of an ultrasonic wave is converted into an image.

As shown in FIG. 1, a measurement sending transducer 7 ($XT_1$ to $XT_N$) and a measurement receiving transducer 9 ($XR_1$ to $XR_N$) face each other across a medium to be measured. Sending and receiving of a measurement continuous wave used for measurement are carried out between the ith elements $XT_i$ AND $XR_i$. Further, in FIG. 1, 1 denotes a timing control portion, 2 a continuous wave oscillator, and 3 a drive amplifier. The oscillator 2 produces a signal that is amplified by sending amplifier 6 to produce a continuous measuring wave. The continuous measuring wave is applied to a multiplexer 8 which switches the wave between sending transducers 7. A pumping wave transducer 5 ($XP_1$ to $XP_M$) sends out a plane pulse wave 16, for example, at a right angle to the continuous-wave beam used for measurement. That is, a delay circuit 4 is provided in the sending circuit and provides a constant delay for triggering of the pulse. When the wave is received by receiving transducers 9, it is multiplexed to a receiving amplifier 11 by multiplexer 10.

It is assumed that the sound pressure of the measurement or probing beam is sufficiently low so that the only pressure variation in the medium is caused by the sound pressure of the plane pulse wave from the pumping transducer 5. If the density of the ultrasonic wave medium is $\rho$, the sound velocity is C, and the equivalent non-linear type parameter is (B/A)e, the sound field C of the measurement beam fluctuates as shown in the following equation (1) due to the sound pressure $\Delta P_0$ of the plane pulse wave.

$$\Delta C = \frac{1}{2\rho C} (B/A)e \cdot \Delta P_0 \quad (1)$$

Therefore, while the plane pulse wave crosses the measurement wave, the phase of the measurement wave at $z = z_0$ varies as follows:

$$\phi(z_0) \approx a \int_{-\infty}^{\infty} * \frac{1}{\rho(z)C(z)} (B/A)e(z)\Delta P \left( \frac{z - z_0}{\bar{C}} \right) dz \quad (2)$$

wherein $\bar{C}$ denotes a mean value of the sound velocity in the medium and a is a proportional constant. Now, considering the following function g(z)

$$g(z_0 - z) = \Delta P \left( \frac{z - z_0}{\bar{C}} \right) \quad (3)$$

then $$\phi(z_0) \approx a \left[ \frac{1}{\rho(z)C(z)} (B/A)e(z) \right] * g(z) \quad (4)$$

wherein * denotes a "convolution". If $G(w) = F\{q(z)\}$ (where F denotes a Fourier Transformation), the distribution on the z axis of $(1/\rho C)(B/A)$ can be calculated or produced by passing the above-mentioned phase variation through a filter having a frequency characteristic of $$\frac{1}{a} \quad \frac{1}{G(w)}$$

That is, the distribution of $(1/\rho C)(B/A)e$ on the measurement or probing continuous-wave beam can be measured or produced by supplying the output of the measurement transmitting transducer $XT_1$ to a phase detector 12 and passing it through the above-mentioned filter 14 after the phase of the output of the transmitting transducer $XT_1$ is detected.

Therefore, repeating the above-mentioned operations by switching the pair of the measurement transducers from $XT_1$, $XR_1$ to $XT_N$, $XR_n$ allows the two-dimensional distribution of $(1/\rho C)(B/A)e$ to be obtained. The information concerning this two-dimensional distribution is stored, for example, in a frame memory 17. A three-dimensional distribution can be obtained by obtaining many two-dimensional distributions with respect to different values for y.

Figure 2:
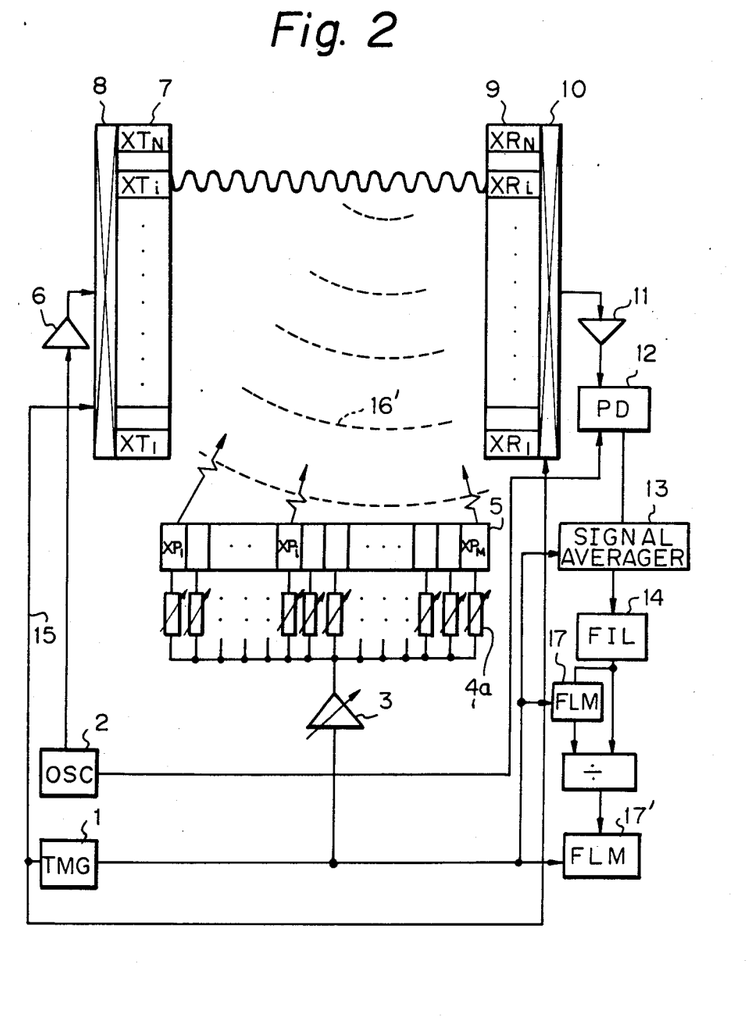
FIG. 2 is a block diagram of an embodiment according to the present invention.

FIG. 2 shows the construction details of the present invention. In FIG. 2, the sending delay circuit 4a is constructed so that the delay amount is suitably applied to the output of the drive amplifier 3.

Figure 3A:
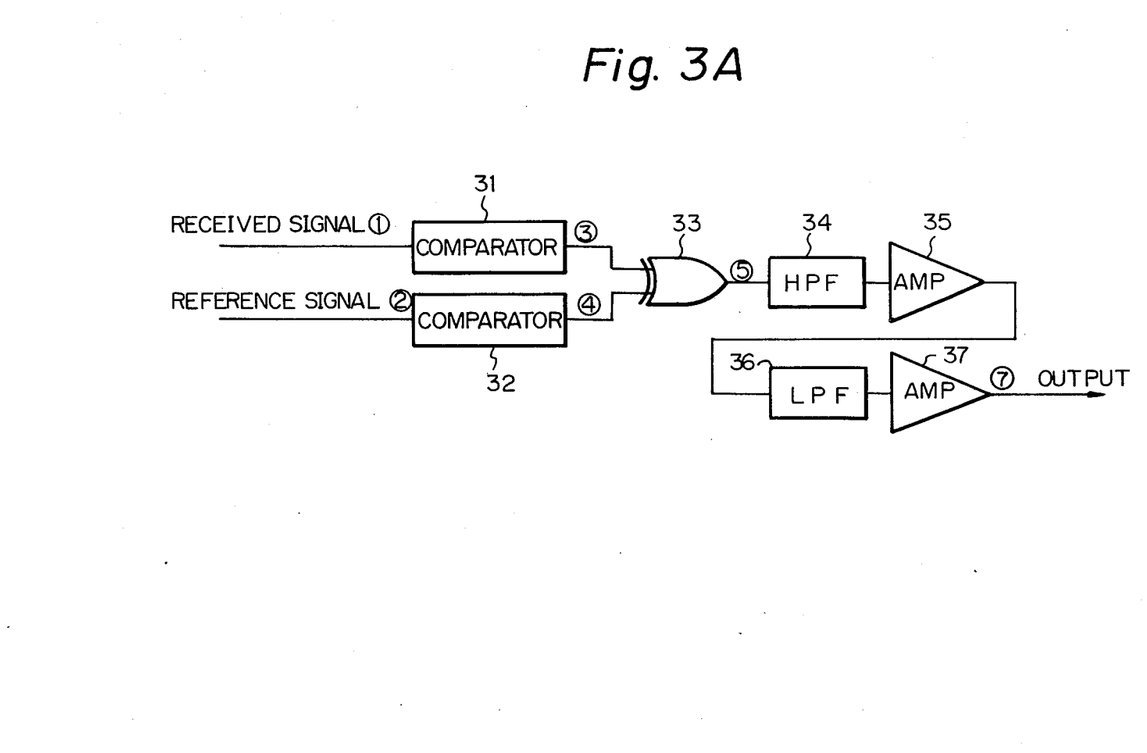
FIG. 3A is a detailed block diagram of a phase detector shown in FIG. 2.
Figure 3B:
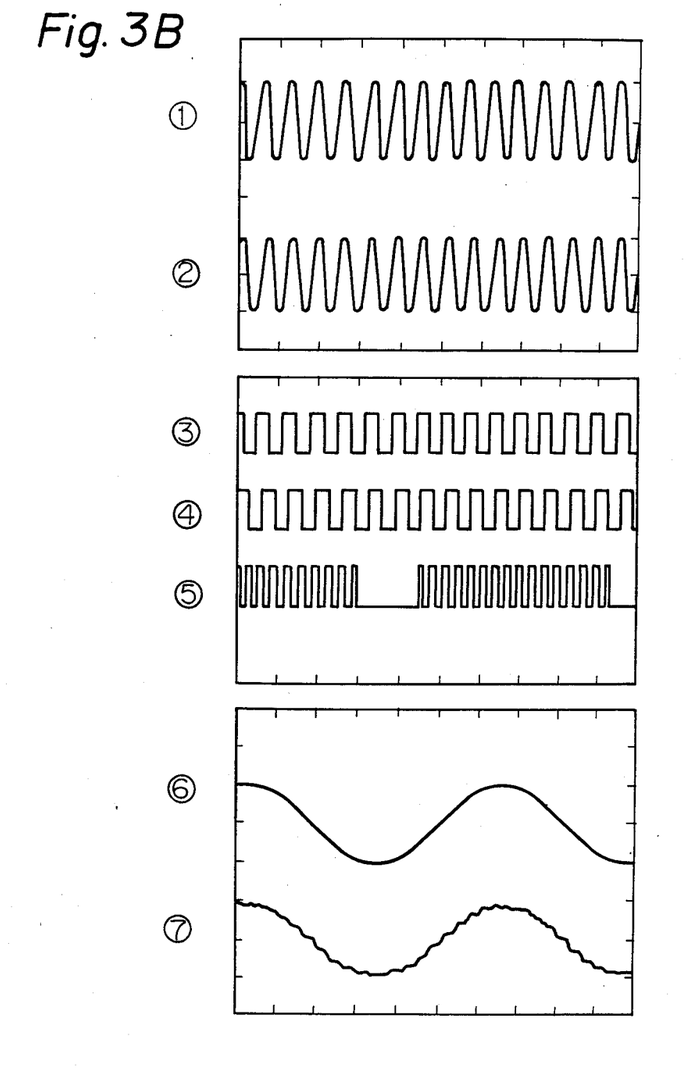
FIG. 3B is a time chart explaining the operation of the phase detector shown in FIG. 2.

The phase detector circuit 12 is constructed as shown in FIG. 3A. In FIG. 3A, comparators 31 and 32 are used for comparing the input of the received signal and the reference signal from oscillator 2 using a threshold value method. That is, the comparators 31 and 32 shown in FIG. 3A extract only phase information (the position information for zero-cross points) from the sinusoidal analog waveforms. In FIG. 3B, ① and ② show the received signal and the reference signal, respectively, and ③ and ④ show the waveforms of the outputs of the comparators 31 and 32, respectively. An exclusive OR circuit 33 outputs the exclusive OR of the waveforms ③ and ④. The output of the exclusive OR circuit 33 is shown in ⑤ of FIG. 3B. In FIG. 3A, a high pass filter 34 removes the slow fluctuations of the phase (such as drift components, for example, variation of the body temperature or atmospheric pressure) and a low pass filter 36 is used for obtaining the amplitude-modulated waveform ⑦ from the pulse-modulated waveform ⑤. The waveform 6 shows the original phase variation.

Figure 4A:
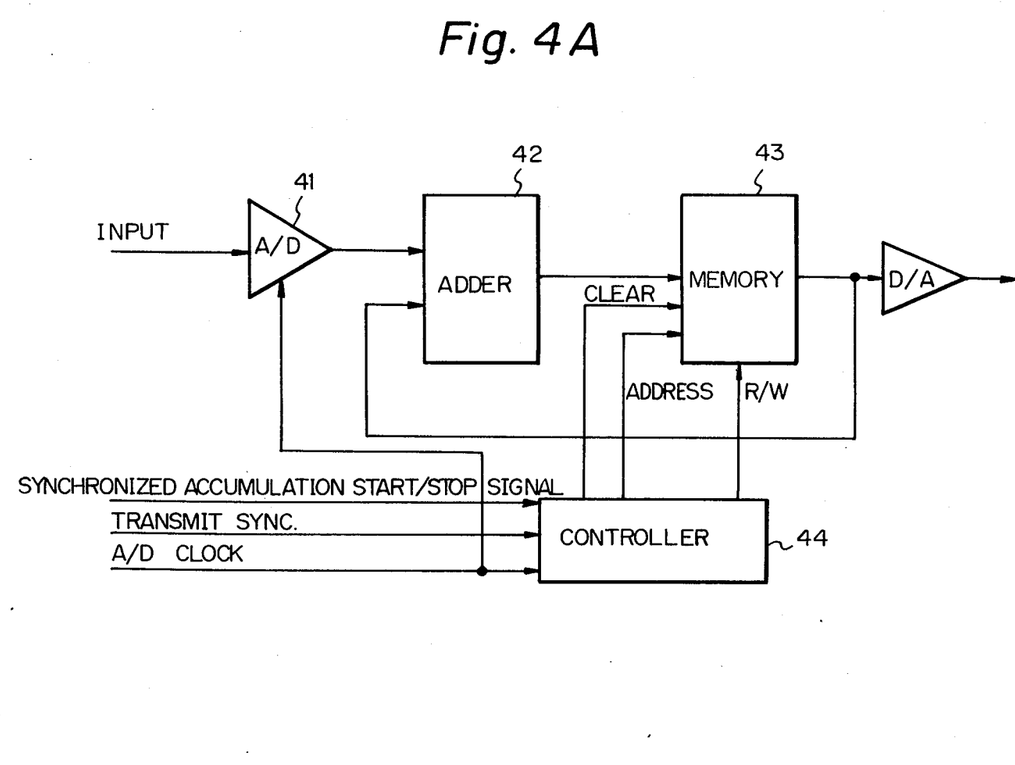
FIG. 4A is a detailed block diagram of a signal averager shown in FIG. 2.

A signal averager 13 is constructed as shown in FIG. 4A and is commercially available. In FIG. 4A, an input signal is converted into a digital signal by an analog-to-digital (A/D) converter 41 and written via an adder 42 into a memory 43. The A/D conversion is carried out as synchronized by an A/D clock. The write and the read of the memory and step up or incrementation of the memory address are carried out by the same A/D clock. The for every pulse of the A/D clock, an A/D conversion, a read-out of the address, an addition of the read-out value and the A/D converted value, a write of the result of the addition into the same address, and a "+1" of the address are carried out. Every time the transmit sync. signal arrives, the above-mentioned operation is commenced from the same starting address (such as, for example, 000 . . . 0 address), that is, the memory address is reset. The above operations continue until the synchronized accumulation commence signal is in the "stop" state.

Figure 4B:
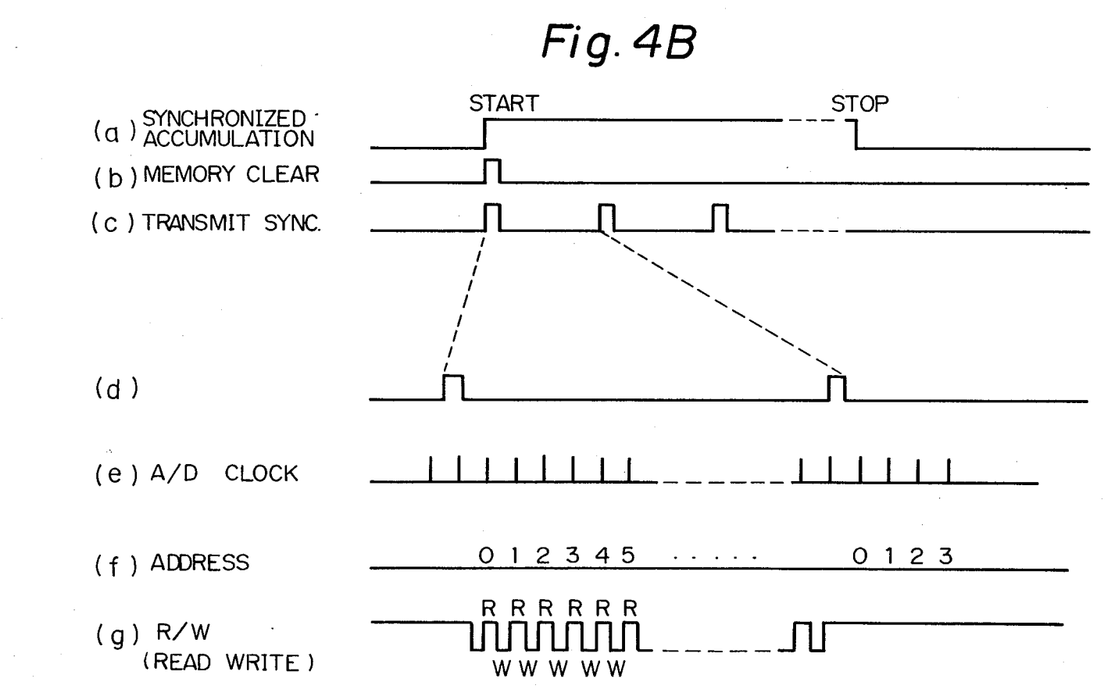
FIG. 4B is a time chart explaining the operation of the signal averager shown in FIG. 2.

In FIG. 4A, a controller 44 receives the synchronized accumulation signal, the transmit sync. signal, and A/D clock and increments the address, provides the read-/write (R/W) control signal, and provides for memory clear at the time when the synchronized accumulation is commenced. FIG. 4B shows the relationships between the synchronized accumulation signal (a), memory clear (b), the transmit sync. (c), and (d), A/D clock (e), the address in the memory (f), and the R/W control (g).

After the synchronized accumulation is completed (or may be during the synchronized accumulation), the average (accumulated) analog waveform is obtained by converting the digital values read out, in order, from the memory into analog values. The synchronized accumulation start and stop and the transmit sync. signal are supplied from the timing control portion 1 shown in FIG. 2.

Figure 5:
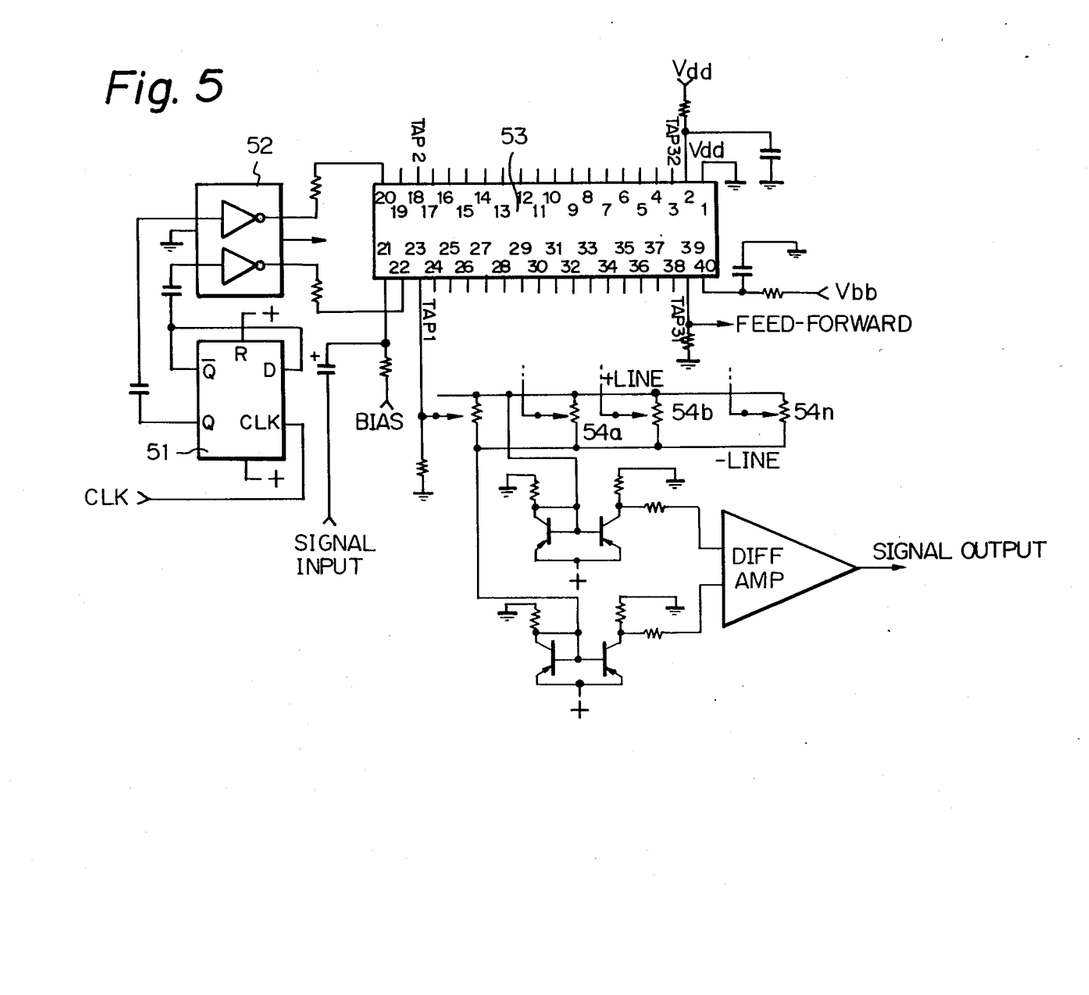
FIG. 5 is a detailed block diagram of a filter shown in FIG. 2.

A filter 14 is constructed as shown in FIG. 5. FIG. 5 is an analog delay circuit TAP-32 of Reticon Co., Ltd. In FIG. 5, the Schottky transistor-transistor logic flip-flop 51 converts the input clock into the desired complementary square wave clock signals at Q and $\bar{Q}$. Rise and fall times are adequately short and skew is minimal. The 0026 translator 53 (produced by National or Motorola) converts the amplitude and the level of those required by the analog delay circuit TAP-32 while preserving the integrity of the waveforms. The output bias and signal summing arrangements for the filter have evolved into the circuit shown in FIG. 5 as the best compromise to conflicting requirements. For equal tap weights, the potentiometers are offset by equal amounts (i.e., resistor values with respect to the + line are all equal, as are the complementary values with respect to the − line; a centered potentiometer gives a zero tap weight); for other filter arrangements, the ratio of the resistances determines the tap weight. In FIG. 5, the input signal to the pin 21 is transmitted from the TAP 1 to TAP 32, and the output of the suitable TAP's are combined at a suitable ratio, so that any filter characteristic can be obtained. In FIG. 5, suitable characteristics for the filter can be obtained by adjusting variohms 54a, 54b ... 54n.

Next, in the circuit shown in FIG. 2, assume that the delay amount between the pumping transducer 4 and the sending delay circuit 4a is suitably provided, so as to obtain a pulse wave 16' having a sound field focus at a certain point. In this case, unlike in the case of the plane wave, the pressure $\Delta P$ of the ultrasonic wave pulse differs in value in accordance with the position. The one-dimensional variation on the measurement beam is given by the following equation for the pressure $\Delta P_0$ of the plane pulse:

$$\phi(z) \approx ak(z) \frac{1}{\rho(z)C(z)}$$

wherein $k(z)$ is a real function of z due to the sound field. Therefore, the phase difference at each point z of the measurement continuous wave is determined from equation (4) as shown below.

$$\phi(z) \approx ak(z) \frac{1}{\rho(z)C(z)} (B/A)e(z)*g(z) \quad (5)$$

If this is passed through the above-mentioned filter, the following is output:

$$\left[ \frac{1}{\rho(z)C(z)} (B/A)e(z) \right] k(z)$$

When this value is divided by the value previously obtained, that is, $$\frac{1}{\rho(z)C(z)} (B/A)e(z)$$

the value $k(z)$ on the measurement beam can be obtained. Therefore, $k(x, z)$, that is, the two-dimensional distribution of the sound field, is obtained by switching the pairs of the measurement transducers so as to obtain $k(z)$. The three-dimensional distribution $k(x, y, z)$ can be obtained by obtaining many images each having a two-dimensional distribution. Further, if the value $\Delta P$ is required, it can be calculated by multiplying the distribution of k by the value of $\Delta P_0$.

Figure 6:
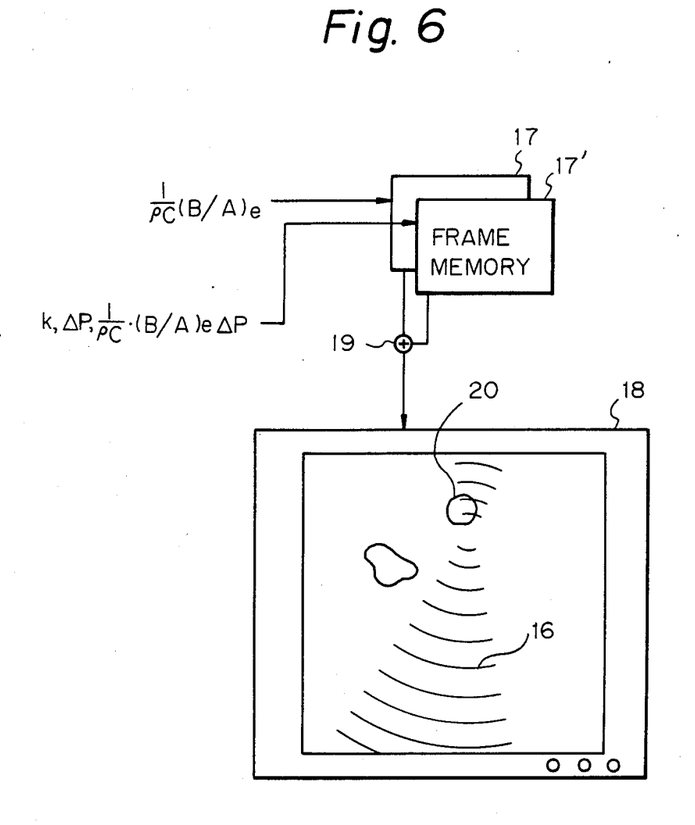
FIG. 6 is a diagram of the application of the present invention.

Next, as shown in FIG. 6, "k" is synthesized and displayed together with $(1/\rho C)(B/A)e$ obtained above. The distribution of k shows the sound field in the ultrasonic wave medium of the pumping transducer 5. By synthesizing and displaying as shown in FIG. 6, the sound field of the pumping transducer 5 can be precisely focused to a target on the picture of $(1/\rho C)(B/A)e$.

In this method, there is a problem of distortion between the actual medium and the picture of $(1/\rho C)(B/A)e$. The picture $(1/\rho C)(B/A)e$ of the measurement pumping pulse wave is distorted from the actual distribution of the medium due to fluctuations in the ultrasonic wave sound velocity. The picture of $(1/\rho C)(B/A)e$ and the picture of k, however, are distorted for the same reason and by the same amount. Therefore, if the focus of k is placed or aimed at a position of a target on the picture $(1/\rho C)(B/A)e$ of the synthesized figure, the same result as if the focus was adjusted to a desired portion of the actual medium can be obtained. Further, the same result can be obtained if the distribution of $\Delta P$ is used instead of the distribution of k. Further, if $$\frac{1}{\rho C} (B/A)e\Delta P, \frac{1}{\rho C} (B/A)ek$$

is used instead of k, the form of the beam can be sufficiently represented.

The focus of the pumping transducer 5 can be adjusted to any arbitrary position by suitably changing the delay amount of the sending delay circuit 4 shown in FIG. 2 or by mechanically moving the pumping transducer 5, that is, the shape or form of the wave can be arbitrarily changed.

This apparatus is very effective in hyperthermia. First, a tumor to be killed is located by the picture $(1/\rho C)(B/A)e$. The focus of the pumping transducer is adjusted at the tumor by using the above-mentioned method. Then, heating is carried out by raising the output of the pumping transducer to kill only the tumor.

The output of the pumping transducer may be raised by increasing only the amplitude of the pulses, as shown in FIG. 2, or by switching the pulse wave to a continuous wave.

The image of the distribution displayed at the same time as the image of the sound field may be converted to a conventional B mode image or tissue characterization image for realization of both a diagnosis apparatus covering a wide range of information and a medical treatment apparatus.

Further, the distribution of FIG. 1 and the distribution of FIG. 2 may be obtained by switching the two-dimensional plane distribution as an unit, however, it may also be obtained by switching one dimensional distribution (that is, the distribution on a straight line by the pairs of $XT_i$, $XR_i$) as a unit and determining the ratio of the same in order to obtain a two-dimensional distribution.

As mentioned above, according to the present invention, the sound field of an ultrasonic wave in an ultrasonic wave medium is converted into a video image and the wave is easily controllable to produce any spatial distribution with comparatively simple means by observing the converted image.

We claim:

1. An apparatus for observing a sound field of an ultrasonic wave, comprising:
   first means for determining a first parameter value of a medium at each point in a predetermined region using a first ultrasonic wave having a sound field of an arbitrary shape transmitted into the medium, the first parameter value being an equivalent second-order acoustic nonlinearity parameter which characterizes the nonlinear relationship between pressure and density in a medium;
   second means for displaying the output of said first means as one of a two-dimensional and a three-dimensional picture of said predetermined region, thereby displaying the shape of the sound field of said first ultrasonic wave;

third means for determining a second parameter value of the medium at each point in said predetermined region using a second ultrasonic wave having a sound field uniform over said predetermined region of the ultrasonic wave field transmitted into the medium, the second parameter value being substantially the same as the first parameter value; and fourth means for determining a ratio of the first and second parameter values of the medium at each point therein obtained from said first and third means, the output of said fourth means being supplied to said second means and displayed thereby.

2. An apparatus for observing a sound field of an ultrasonic wave according to claim 1, further comprising an ultrasonic wave vibrator for said medium and wherein said first means detects a space distribution of $(1/\rho C)(B/A)e \cdot \Delta P$, which is the product of a pressure change $\Delta P$ caused by an ultrasonic wave pulse from the ultrasonic wave vibrator which generates a sound field having an arbitrary form in said medium of the ultrasonic wave and an amount $(1/\rho C)(B/A)e$ determined by the medium of the ultrasonic wave, where $\rho$ is a density of the medium, C is sound velocity in the medium and $(B/A)e$ is a non-linear parameter value of the medium.

3. An apparatus for observing a sound field of an ultrasonic wave according to claim 2, wherein said second means displays a distribution of the pressure change $\Delta P$ caused by an ultrasonic pulse from said ultrasonic wave vibrator based on $(1/\rho C)(B/A)e$ and $(1/\rho C)(B/A)e \cdot \Delta P$.

4. An apparatus for displaying an ultrasonic sound wave in a medium, comprising:

means for transmitting a probing wave into the medium;

means for transmitting a pumping wave into the medium;

means for converting a received wave which is the probing wave modified by the pumping wave into a display of the medium and the pumping wave.

5. An apparatus according to claim 4, further comprising means for modifying the shape of the pumping wave.

6. An apparatus according to claim 4, further comprising means for focusing the pumping wave.

7. An apparatus for observing a sound field of an ultrasonic wave in a medium, comprising:

first means for determining a first parameter value of the medium at each point in a predetermined region using a first ultrasonic wave having a uniform sound field transmitted into the medium and detecting the field produced therefrom, the first parameter value being an equivalent second-order acoustic nonlinearity parameter which characterizes the nonlinear relationship between pressure and density in a medium;

second means for displaying the output of said first means as one of a two-dimensional and a three-dimensional picture of the predetermined region to display the shape of the sound field of the first ultrasonic wave; and means for determining a second parameter value of the medium, substantially the same as the first parameter value, at each point in the predetermined region of the medium in which the uniform sound field has been provided by using a sound field of an arbitrary shape and said second means displaying the second parameter value.

* * * * *